US00PP13341P2

(12) United States Plant Patent
Kobayashi

(10) Patent No.: US PP13,341 P2
(45) Date of Patent: Dec. 10, 2002

(54) POINSETTIA PLANT NAMED 'ECKALOHA'

(75) Inventor: Ruth Kobayashi, Carlsbad, CA (US)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 09/968,333

(22) Filed: Sep. 30, 2001

(51) Int. Cl.[7] ..... A01H 5/00
(52) U.S. Cl. ..... Plt./303
(58) Field of Search ..... Plt./303

(56) References Cited

U.S. PATENT DOCUMENTS

PP11,880 P2 * 5/2001 Fruehwirth ..... Plt./306

OTHER PUBLICATIONS

UPOV ROM GTITM Computer Database, GTI Jouve Retrieval Software 2002/02, Citation(s) for 'Eckaloha'.*

* cited by examiner

*Primary Examiner*—Bruce R. Campell
*Assistant Examiner*—W C Baker
(74) *Attorney, Agent, or Firm*—C. A. Whealy

(57) ABSTRACT

A new and distinct cultivar of Poinsettia plant named 'Eckaloha', characterized by its inflorescences with irregularly lobed pale yellow and pink bi-colored flower bracts; irregularly lobed green and dark green bi-colored leaves; uniform, compact and mounded plant habit; very early flowering; and excellent post-production longevity.

2 Drawing Sheets

BOTANICAL CLASSIFICATION

*Euphorbia pulcherrima.*

BACKGROUND OF THE INVENTION

The present Invention relates to a new and distinct cultivar of Poinsettia plant, botanically known as *Euphorbia pulcherrima* Willd., and hereinafter referred to by the name 'Eckaloha'.

The new Poinsettia a product of a planned breeding program conducted by the Inventor in Encinitas, Calif. The objective of the breeding program is to create new Poinsettia cultivars having flower bracts with desirable colors, uniform plant habit and excellent post-production longevity.

The new Poinsettia is a naturally-occurring whole plant mutation of a unnamed proprietary induced mutation, not patented, that originated by exposing unrooted cuttings of the *Euphorbia pulcherrima* Willd. cultivar Eckabri, disclosed in U.S. Plant Pat. No. 11,880, to gamma radiation. The new Poinsettia was discovered and selected by the Inventor as a single plant within a population of plants of the irradiated selection on or about Mar. 19, 1999, in a controlled environment in Encinitas, Calif.

Asexual reproduction of the new Poinsettia by terminal cuttings taken at Encinitas, Calif., since 1999, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Eckaloha'. These characteristics in combination distinguish 'Eckaloha' as a new and distinct cultivar:

1. Inflorescences with irregularly lobed pale yellow and pink bi-colored flower bracts.

2. Irregularly lobed green and dark green bi-colored leaves.

3. Uniform, compact and mounded plant habit.

4. Very early flowering, natural season flower maturity date is November 18 for plants grown in Encinitas, Calif.; response time, about 7.5 weeks.

5. Excellent post-production longevity.

Plants of the new Poinsettia can be compared to plants of the cultivar Eckabri. In side-by-side comparisons conducted in Encinitas, Calif., plants of the new Poinsettia differed primarily from plants of the cultivar Eckabri in the following characteristics:

1. Leaves of plants of the new Poinsettia were irregularly lobed and green and dark green bi-colored whereas leaves of plants of the cultivar Eckabri were oak-leaf shaped and solid dark green.

2. Flower bracts of plants of the new Poinsettia were irregularly lobed and pale yellow and pink bi-colored whereas flower bracts of plants of the cultivar Eckabri were oak-leaf shaped and solid pink in color.

Plants of the new Poinsettia are most similar to plants of the cultivar Eckaiden, disclosed in U.S. Plant Pat. No. 11,888. In side-by-side comparisons conducted in Encinitas, Calif., plants of the new Poinsettia differed primarily from plants of the cultivar Eckaiden in the following characteristics:

1. Leaves of plants of the new Poinsettia were irregularly lobed and green and dark green bi-colored whereas leaves of plants of the cultivar Eckaiden were oak-leaf shaped and solid dark green in color.

2. Plants of the new Poinsettia flowered about one week earlier than plants of the cultivar Eckaiden.

3. Flower bracts of plants of the new Poinsettia were irregularly lobed whereas flower bracts of plants of the cultivar Eckaiden were oak-leaf shaped.

4. Flower bracts of plants of the new Poinsettia had larger and darker pink centers than flower bracts of plants of the cultivar Eckaiden.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type. Colors in the photographs may differ slightly from the color values cited in the detailed botanical description which accurately describe the colors of the new Poinsettia.

The photograph on the first sheet comprises a side perspective view of a typical flowering plant of 'Eckaloha' grown in a 16.5-cm container.

The photograph at the top of the second sheet comprises a top perspective view of a typical flowering plant of 'Eckaloha'. The photograph at the bottom of the second sheet is a close-up view of typical leaves and flower bracts of 'Eckaiden' (top) and 'Eckaloha' (bottom).

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype.

The aforementioned photographs, following observations and averaged measurements describe plants grown in Encinitas, Calif. during the winter under commercial practice in a polyethylene-covered greenhouse with day temperatures about 24° C., night temperatures about 19° C., and light levels about 4,000 foot-candles. Single plants were grown in 16.5-cm pots and pinched once. Plants were flowered under natural season short day/long night conditions. Plants were about 16.5 weeks from unrooted cuttings when the photographs and the detailed botanical description were taken.

In the following description, color references are made to The Royal Horticultural Society Colour Chart except where general terms of ordinary dictionary significance are used.

Botanical classification: *Euphorbia pulcherrima* Willd. cultivar Eckaloha.

Parentage: Naturally-occurring whole plant mutation of an unnamed proprietary *Euphorbia pulcherrima* Willd. induced mutation, not patented.

Propagation:

*Type cutting.*—Terminal cuttings.

*Time to initiate roots.*—About 10 days at 20 to 22° C.

*Time to develop roots.*—About 28 days at 20 to 22° C.

*Root description.*—Thick, fibrous and freely-branching.

Plant description:

*Plant form.*—Inverted triangle, top of plant rounded and mounding.

*Growth habit.*—Upright and uniform plant habit; relatively compact. Moderate vigor.

*Plant height.*—About 25 cm.

*Plant diameter or spread.*—About 30 cm.

*Lateral branch description.*—Quantity: About seven lateral branches develop after pinching. Length: About 19 cm. Diameter: About 5 mm. Internode length: About 2.3 cm. Color: 146A, slightly overlain with 59B.

*Foliage description.*—Arrangement: Alternate, single. Quantity of leaves per lateral branch: About six. Length: About 10.5 cm. Width: About 9 cm. Shape: Deltoid with irregular lobing. Apex: Narrowly acute. Base: Acute. Margin: Entire with irregular lobing. Venation pattern: Pinnate. Texture: Upper surface: Glabrous. Lower surface: Slightly pubescent. Surface: Undulate, rugose and twisting. Color: Young foliage, upper surface: Ground color, 137A, interspersed with random spots and areas of 147A. Young foliage, lower surface: 137A. Fully expanded foliage, upper surface: Ground color, 137A, interspersed with random spots and areas of 147A. Fully expanded foliage, upper surface: 137B. Venation, upper surface: 147C. Venation, lower surface: 147D. Petiole: Length: About 4.25 cm. Diameter: About 2 mm. Color: 179B.

Inflorescence description:

*Inflorescence type and habit.*—Inflorescences are compound corymbs of cyathia with colored flower bracts subtending the cyathia. Inflorescences are not fragrant. Inflorescences persistent.

*Natural flowering season.*—Autumn/winter in Northern Hemisphere. Flower initiation and development is induced under long nyctoperiod conditions. Response time, about 7.5 weeks; natural season flower maturity date is November 18 for plants grown in Encinitas, Calif.

*Post-production longevity.*—Plants of the new Poinsettia maintain good substance and bract color for about four weeks under interior conditions.

*Quantity of inflorescences per plant.*—One per lateral branch, about six.

*Inflorescence size.*—Diameter: About 26 cm. Height (depth): About 4.25 cm.

*Flower bracts.*—Quantity: About 26 bracts per inflorescence. Length, largest bracts: About 10 cm. Width, largest bracts: About 7.5 cm. Shape: Deltoid with irregular lobing. Apex: Narrowly acute. Base: Acute. Margin: Entire with irregular lobing. Texture, upper and lower surfaces: Glabrous, velvety. Surface: Concave, rugose. Orientation: Mostly horizontal. Color: Developing or transitional bracts, upper surface: Irregular and random areas of 52A and 5D and 137A, then becoming mostly 52A at the center surrounded by 5D. Developing or transitional bracts, lower surface: Irregular and random areas of 50A and 5D and 137B, then becoming mostly 50A at the center surrounded by 5D. Fully developed bracts, upper surface: Center, 51A, surrounded by 5D; pink centers fading to 51C with subsequent development. Oldest bracts may be entirely pink or with small areas of pale yellow at the margins. Fully developed bracts, lower surface: Center, 51B, surrounded by 5D. Venation, upper and lower surfaces: Same as ground color. Bract petiole: Length: About 2.5 cm. Diameter: About 1.5 mm. Color: 50B.

*Cyathia.*—Quantity: About 20 per corymb. Diameter of cyathia cluster: About 3.5 by 4 cm. Length: About 7 mm. Width: About 4 mm. Shape: Ovoid. Color, immature and mature: 145A. Peduncle: Length: About 1.5 mm. Diameter: Less than 1 mm. Aspect: Strong, erect. Color: 145A. Stamens: About 15 sterile stamens per cyathium. Pistils: None observed. Nectary number: One per cyathia. Nectary color: 23A.

Disease/pest resistance: Resistance to pathogens and pests common to Poinsettias has not been observed on plants grown under commercial conditions.

It is claimed:

1. A new and distinct cultivar of Poinsettia plant named 'Eckaloha', as illustrated and described.

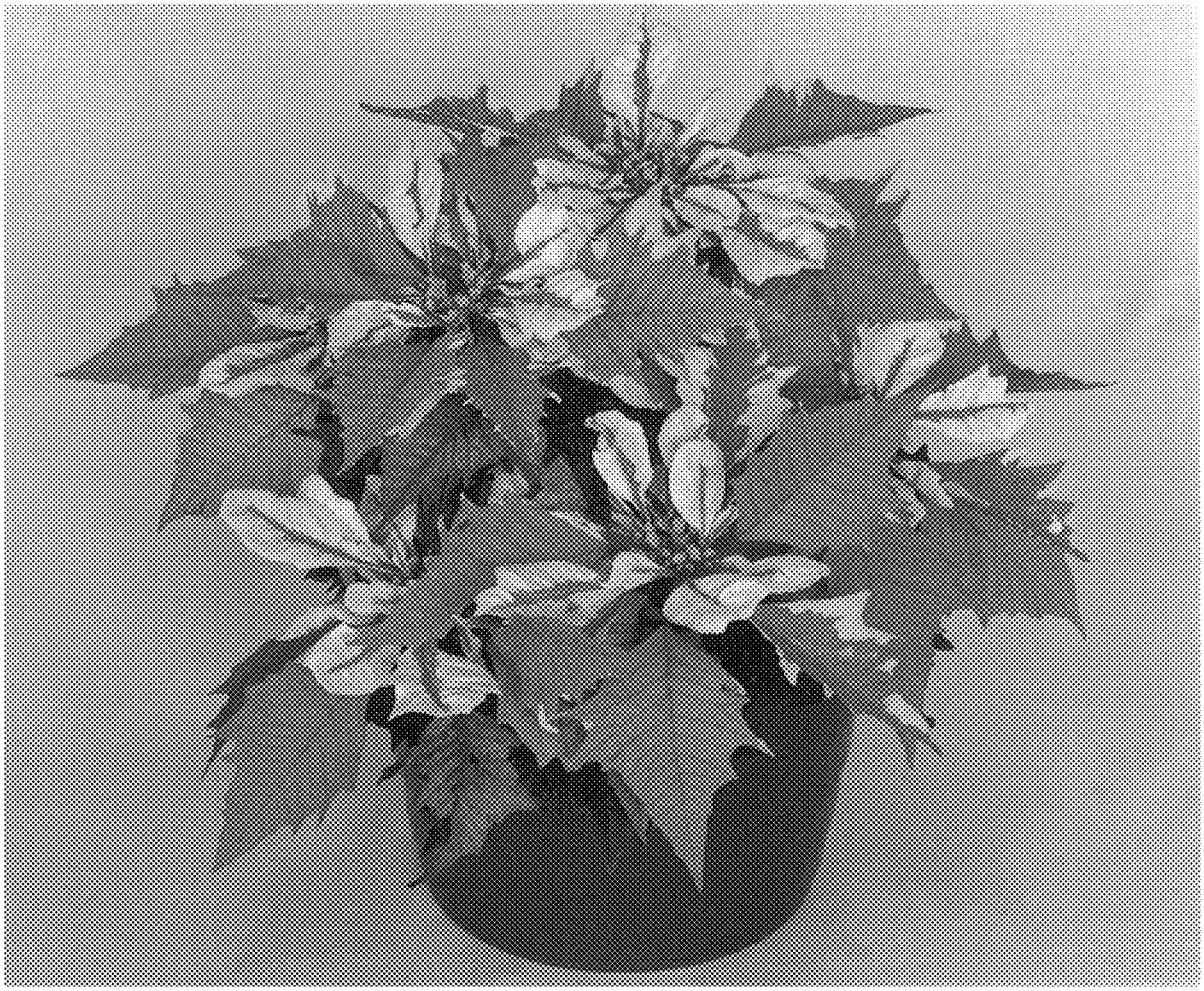

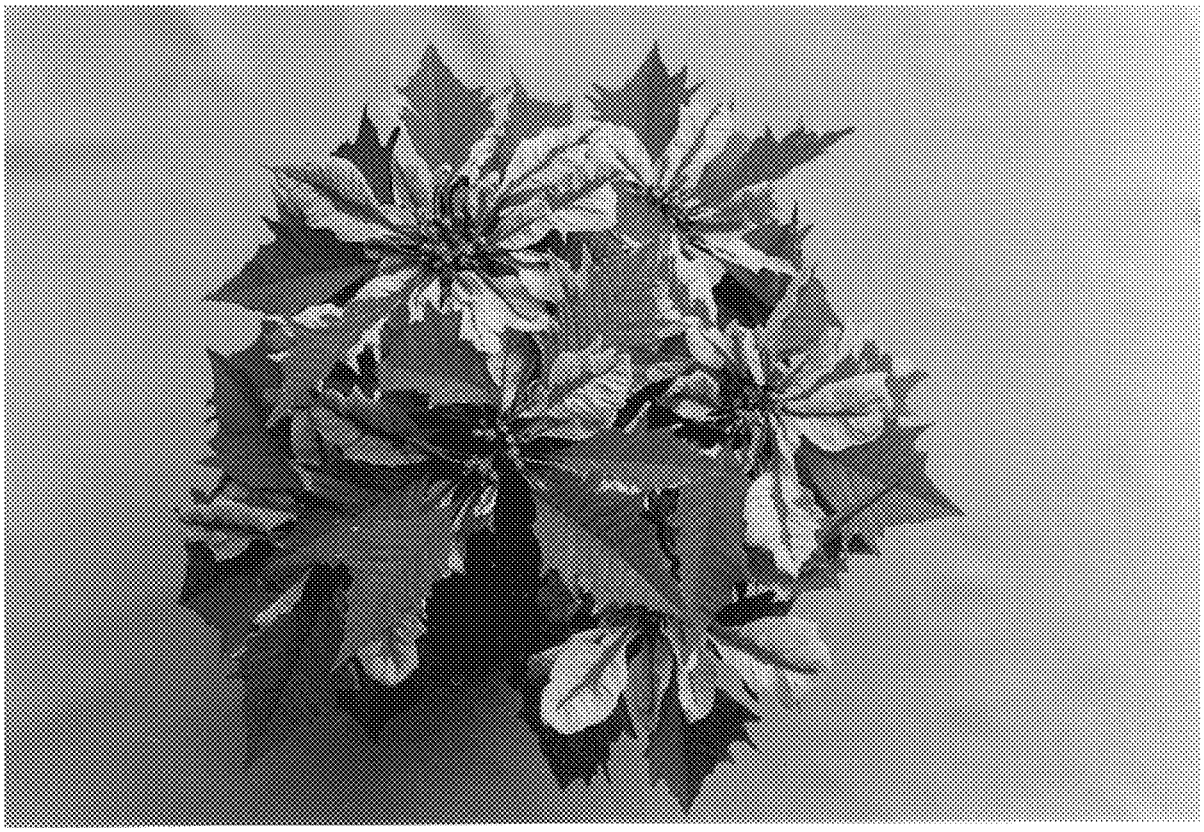
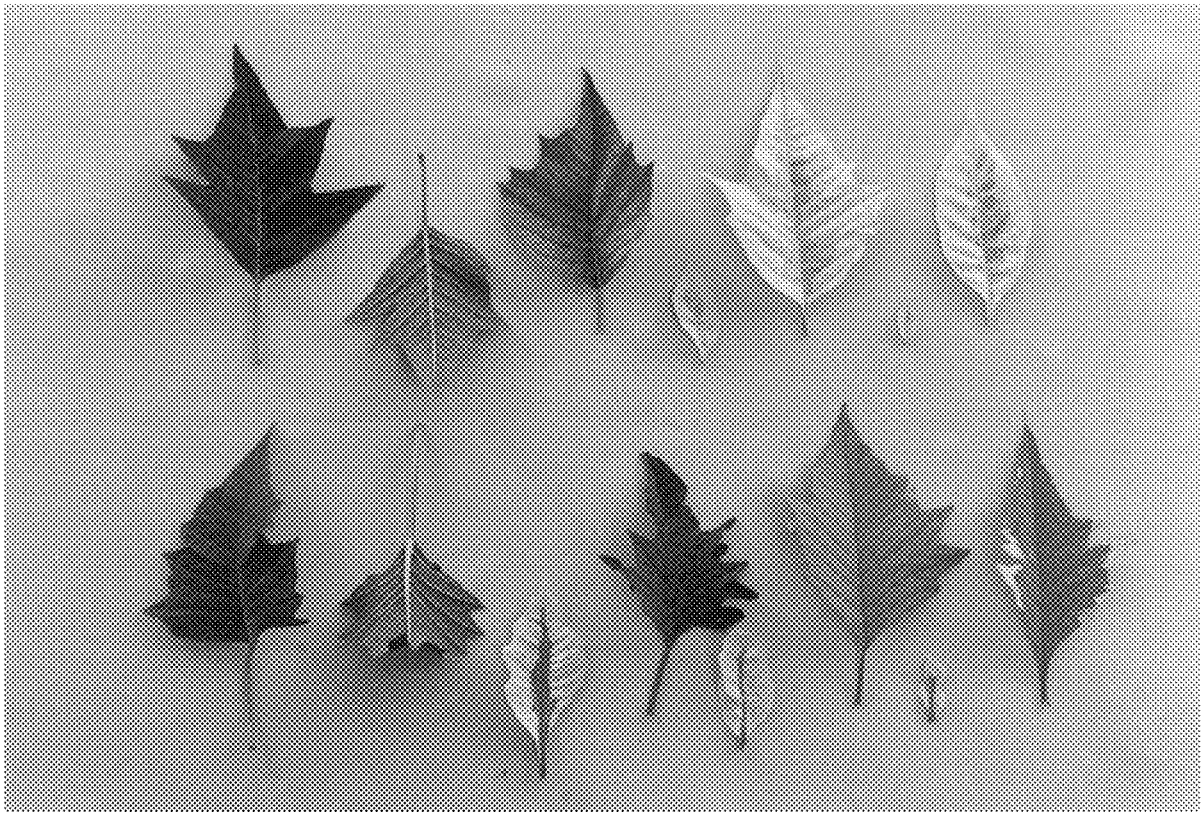

* * * * *